US008585737B2

(12) United States Patent
Moehrle (10) Patent No.: US 8,585,737 B2
(45) Date of Patent: Nov. 19, 2013

(54) DEVICE FOR STRETCHING REGIONS OF TISSUE (75) Inventor: Matthias Moehrle, Tuebingen (DE)

(73) Assignee: Karl Storz GmbH & Co. KG (DE)

( * ) Notice: Subject to any disclaimer, the term of this patent is extended or adjusted under 35 U.S.C. 154(b) by 322 days.

(21) Appl. No.: 12/845,288

(22) Filed: Jul. 28, 2010

(65) Prior Publication Data
US 2011/0040325 A1 Feb. 17, 2011

(30) Foreign Application Priority Data

Jul. 28, 2009 (DE) .......................... 10 2009 036 165

(51) Int. Cl.
A61B 17/08 (2006.01)
(52) U.S. Cl.
USPC .......................................... 606/216; 606/215
(58) Field of Classification Search
USPC .................................. 606/215–218, 232–233
See application file for complete search history.

(56) References Cited

U.S. PATENT DOCUMENTS

| 4,535,772 | A | 8/1985 | Sheehan |
| 5,127,412 | A | 7/1992 | Cosmetto et al. |
| 6,120,525 | A | 9/2000 | Westcott |
| 6,471,715 | B1 | 10/2002 | Weiss |
| 2004/0193187 | A1* | 9/2004 | Boehringer et al. .......... 606/144 |
| 2004/0254609 | A1 | 12/2004 | Esplin |
| 2006/0095076 | A1* | 5/2006 | Elliott et al. .................. 606/216 |
| 2006/0229676 | A1 | 10/2006 | Doll et al. |
| 2007/0255315 | A1 | 11/2007 | Buckman et al. |
| 2008/0147115 | A1* | 6/2008 | O'Malley et al. ............. 606/216 |
| 2010/0137817 | A1* | 6/2010 | Hardman et al. ............. 604/290 |

FOREIGN PATENT DOCUMENTS

| DE | 7137754 U | 1/1972 |
| DE | 10349953 A1 | 6/2005 |
| DE | 69918948 T2 | 7/2005 |
| WO | 9935974 A1 | 7/1999 |

OTHER PUBLICATIONS

Nabil A A et al: Closure of large abdominal wounds with an adjustable suture-tension device 1 in Journal of the American College of Surgeons, Aug. 2002, vol. 195, Issue 2, pp. 281-283.
Barnea Y et al: Delayed primary closure of fasciotomy wounds with Wisebands, a skin- and solft tissue-stretch device in Injury, Jun. 2006; 37(6): 561-566.

* cited by examiner

Primary Examiner — Dianne Dornbusch
Assistant Examiner — Robert Lynch
(74) Attorney, Agent, or Firm — St. Onge Steward Johnston & Reens LLC (57) ABSTRACT A device for stretching regions of tissue has at least one first plate-like body and at least one second plate-like body. At least one pulling thread joins the plate-like bodies. One tensioning device is arranged on at least one of the plate-like bodies and is connected to the pulling thread for applying a tensile force to the pulling thread. A guidance serves for guiding the at least one pulling thread during a movement of the at least two plate-like bodies towards one to another.

17 Claims, 3 Drawing Sheets

DEVICE FOR STRETCHING REGIONS OF TISSUE

BACKGROUND OF THE INVENTION

The invention relates to a device for stretching regions of tissue.

The stretching of tissue, in particular of skin tissue, is a process that is often carried out in surgery, in particular in plastic surgery.

Apart from stretching skin, stretching of connective tissue, tendons, muscles and also of vessels takes place.

In dermatological surgery, in particular in plastic-reconstructive surgery, stretching of the skin on both sides of lesions is required before the removal of the lesion.

The excision or removal of lesions sometimes involves the removal of skin tumours, birthmarks or moles or else scars over a large surface area.

If such a lesion is relatively large in area, it cannot be removed by a single intervention, since the regions of the skin around the lesion must be greatly stretched, the stretching producing a restoring force which disturbs the healing of the wound or has the tendency to tear open again the usually sewn site of the operation. Therefore, so-called serial excisions have been used in the past. This means that initially only parts of a lesion are removed. Time until the surrounding skin has stretched back is then allowed to pass, which generally takes months, in order then to remove a further part of the lesion and also the scar of the previous operation.

This procedure is not only very laborious but also, for the patient, involves corresponding repeated stress and strain, risks, costs and, for example, incapacity to work.

So-called tissue expanders that are implanted under the surrounding skin have been developed. Once the wound has healed, the tissue expander is gradually filled with liquid transcutaneously. The "water balloon" created in this way stretches out the surrounding skin. After some weeks, the expander can be removed. The lesion is thereby excised and the defect is covered with the skin obtained by expansion.

Such tissue expanders are very expensive and can only be used once. The procedure has a high risk of infection, since a foreign body that often punctures and has to be refilled has to be implanted under the skin. Frequent appointments with highly specialized doctors are thereby necessary, for the operation and for filling the tissue expanders. The filled balloon is clearly visible and restricts the private and professional life of the patient for weeks.

DE 103 49 953 B4 discloses a device for fixing and tensioning at least one pulling thread for applying a neovagina. This device comprises a plate-like base body on which at least one fixing element for fixing the at least one pulling thread under tension is arranged, the fixing element being assigned a spring, the first end of which is fixed to the base body. For the tensioning of the at least one pulling thread, the fixing element can be turned about an axis of rotation, a locking device being provided for the fixing element, by means of which device the fixing element can be locked at least in a direction of rotation opposite the direction of rotation for tensioning the at least one pulling thread. The free end of the pulling thread, or optionally a number of pulling threads, is joined to a plastic olive or so-called phantom. These exert a continuous pressure on the vaginal dimple by way of the tensile force, whereby a neovagina is formed within several days.

It is an object of the present invention to achieve rapid tissue stretching within a short time using the minimally invasive surgical technique.

SUMMARY OF THE INVENTION

According to the invention, the object is achieved by a device for stretching regions of tissue by said device having at least one first plate-like body and at least one second plate-like body, which can be arranged lying opposite on the tissue, there being at least one pulling thread which joins the two plate-like bodies to one another, and by said device having at least one tensioning device on at least one of the two plate-like bodies, for applying a tensile force to the at least one pulling thread, whereby the plate-like bodies can be moved towards one another, and thread guidance, by means of which the two plate-like bodies can be joined together in such a way that they are fixed in terms of tensile force.

These measures then have several advantages.

The two plate-like bodies are arranged lying opposite on the tissue, for example on both sides of a lesion on the skin that is to be excised. That is to say that they do not have to be implanted in or under the tissue.

The two plate-like bodies are configured in such a way that they can be joined together by means of the pulling thread.

The thread guidance may advantageously take place by the respective plate-like body being fixed to the tissue by the thread, and by the plate-like bodies at the same time being joined to one another by means of the thread. This may be carried out by a simple procedure with an appropriate awl, i.e. the thread may be fixed at one end to the first plate-like body and guided through the tissue to the opposite, second plate-like body. The free end of the thread is joined to the tensioning device, by means of which a tensile force is exerted on the thread. This tensile force causes the two plate-like bodies to move towards one another. As a result, the tissue situated between the opposite edges of the plates is compressed; the region of tissue situated "behind" the plate-like bodies, seen in the direction of movement of the two plate-like bodies, is thereby stretched.

The surface and the shaping of the plate-like bodies may be chosen such that already as a result of this they come into tensile-force-transmitting engagement with the tissue. This includes projections, nubs, flutings, etc. It is then possible in principle to dispense with fixing of the plate-like bodies to the tissue by the pulling thread.

Fixing the plate-like bodies to the tissue has the effect that the plate-like bodies are firmly held on the tissue, so that the patient can move freely. Since the thread is guided through the tissue from the one plate-like body to which it is fastened to another plate-like body, and is joined at the other end to the tensioning device, a tensile force which causes the two plate-like bodies to be moved towards one another can be exerted on the thread by means of this tensioning device.

The controlling and observing of these displacement processes can be easily carried out from the outside, since all the components lie on the tissue; only the joining by means of the thread takes place through the tissue.

From the technical aspect of the surgery, this has the considerable advantage that the setting of the thread is a procedure that can be carried out very easily and entails an extremely low risk of infection. Consequently, the setting of the plate-like bodies can, for example, be carried out by a doctor in the course of outpatient treatment within a short period of time.

The procedure of tensioning the thread and controlling it to the effect that the two plate-like bodies are gradually moved towards one another over several days can also be carried out by the patient his/herself.

For this purpose, said patient receives from the treating doctor a specific plan as to how often and how much the tensioning device must be actuated, which may, for example, simply take place by the tensioning device having an adjusting wheel around which the thread is wound up.

If, for example, the basic principle of DE 103 49 953 A1, cited at the beginning, with respect to the tensioning device is used, there is a latching mechanism there, by means of which the tensioning wheel can be turned in each case over a certain number of detents, the thread then being correspondingly tensioned, with the consequence that in the present invention the two plate-like bodies are moved somewhat towards one another. It is therefore possible to give the patient a plan specifying in which time intervals and in which increments the two plate-like bodies should be moved towards one another until the appropriate stretching of the skin or compression in the region of the lesion has taken place, which may take place within several days.

Only then does the patient have to attend an appointment again, in which the tissue is removed, the wound is closed and the device is removed again.

When the plate-like bodies are lying on both sides of a lesion on the skin, the lesion (for example a scar or mole) can be removed.

The region of tissue compressed between the plate-like bodies may also be used for obtaining tissue, for example for building up a breast after an Ablatio mammae.

On the one hand, tissue may be stretched and, on the other hand, a surface area and volume of tissue between the plate-like bodies may be obtained for reconstructions.

The term plate-like body should be understood in the sense that there is a two-dimensional contact region for placing against and optionally fixing on the tissue and that, when the at least one pulling thread is tensioned, the bodies move towards one another, build up compressed tissue between them and stretch the tissue "behind" in the pulling direction or direction of movement.

Seen overall, the stretching process and the removal of the tissue can consequently be carried out very easily and with scarcely any adverse effect, by few interventions and with a low risk of infection for the patient.

The plate-like bodies can be used repeatedly, since such bodies are easy to clean, disinfect and sterilize. The shape, size, thickness and materials of the plate-like bodies may be respectively chosen such that they are most suitable for the corresponding area of use on the tissue and are compatible for the patient.

If a lesion is present in a flat region of skin of a large surface area, for example in the region of the breast or back, the plate-like bodies may be of a planar and relatively large form.

If the lesion is on regions of the skin with great curvatures, such as for example on the arm and legs, or at very sensitive locations, for example in the region of the head, plate-like bodies that are correspondingly small, lightweight and adapted to the curvature may then be provided.

The basic principle always remains the same; the plate-like bodies can be applied to the tissue, optionally fixed and joined together.

The two plate-like bodies must be anchored to the tissue in order that the tensile force that acts on the thread is opposed by an abutment that provides the conversion of the tensile force into the movement directed towards one another. The thread guidance may be such that the at least one pulling thread not only joins the plate-like bodies together but also at the same time fixes them to the tissue. The anchorage of the plate-like bodies may also be performed by clips, so that the pulling thread only joins the two plate-like bodies to one another.

If, for example, the plate-like bodies are attached to the skin on both sides of a lesion and are joined together subcutaneously, adequate stretching of the skin can already be achieved within a few days by regular actuation of the tensioning device. The structural design allows a very flat construction, so that for example the device can be scarcely seen from the outside when it is placed on locations of the body that are usually covered by clothing. This contributes considerably to so-called patient compliance, and consequently also to the success of a simple and uncomplicated excision of the lesion. The regions of skin in the region of the lesion that are compressed between the plates to be moved towards one another make it easier for the doctor also to remove these regions of skin, since the compression already has the effect that they are brought together from a two-dimensional base into a more linear structure. Consequently, the actual intervention is also made easier as a result.

In a further configuration of the invention, the thread guidance on the plate-like body that lies opposite the tensioning device has at least two abutments spaced laterally apart from one another.

This measure has the advantage that the tensile force on this plate-like body does not just act at one point, which could gradually lead to turning during the displacement of this plate-like body, but instead a tensile force is exerted as a result of the abutments spaced laterally apart from one another, with the effect that the plate-like body is moved towards the opposite plate-like body in a more rectilinear movement.

As a result, dependable rectilinear control of the movement is possible, so that it is not necessary to check periodically whether the plate-like body is also following the desired path of movement. This multi-point contact by way of the number of abutments also has the advantage that the tensile forces can be transmitted more uniformly by way of the plate-like body and the thread into the tissue, so that the least traumatic possible stretching of tissue takes place.

In a further configuration of the invention, the thread guidance on the plate-like body that carries a tensioning device has at least one guiding location by means of which the thread can be fed to the tensioning device and can be wound up there at a first end.

This measure has the advantage that, as a result, the arrangement of the tensioning device on the corresponding plate-like body can as such be freely selected, i.e. where it is most favourable, since the guiding location has the effect that the thread is in each case guided specifically to the tensioning device.

In a further configuration of the invention, the device also has on the plate-like body that carries a tensioning device a fixing location for the other end of the thread.

This measure has the advantage that both ends of the pulling thread are anchored on this one plate-like body, that is to say on the one hand at the fixing location and on the other hand at the tensioning device. This makes handling easier to the extent that the thread is, for example, fixed at one end to this plate-like body, then guided through the tissue, for example subcutaneously, to the opposite plate-like body, acting as a counterpart, and is then guided by the latter body back again to the tensioning device.

In interaction with a counterpart with an appropriate number of anchoring locations, particularly specific and dependable guidance of the two plate-like bodies is then possible during the movement directed towards one another.

In a further configuration of the invention, for this purpose the abutments on the one plate-like body and the guiding location and the fixing location on the other plate-like body lie at the corners of a quadrilateral.

This configuration has the advantage that, when the thread is tensioned, the oppositely lying plate-like bodies are moved towards one another in an exactly directed manner. Thus, for example, the four corner points may lie at the corners of a more or less geometrically exact rectangle, so that the two plate-like bodies are moved towards one another in an exactly rectilinear manner. In the removal of a mole, which usually has a round contour, in the case of this configuration the two plate-like bodies may be placed diametrically opposite at the ends of the mole, fixed to the skin and joined together. After the stretching of the skin, the mole is correspondingly compressed or squeezed between the two plate-like bodies, the stretching taking place along a diameter that is offset approximately by 90° in relation to the diameter that lies in the direction of movement directed towards one another.

In a further configuration of the invention, the abutments, the fixing location and the guiding location are formed as openings in the plate-like bodies, by means of which the at least one pulling thread can be guided transversely through the plane of the plates.

This measure has the advantage that such openings can be easily produced in such plate-like bodies and also can be cleaned, disinfected and sterilized well. It is likewise very easy for handling; for example, the doctor starts from an opening on one plate-like body and inserts an awl to which the thread is fastened into the tissue, for example into the skin, guides the thread subcutaneously through as far as the corresponding opposite location and brings it through the skin again to the outside.

He can then thread the second plate-like body onto the point emerging from the skin, by guiding the point of the awl together with the thread, or the thread alone, through this opening. He then repeats this procedure by returning the thread again to the other plate-like body and then guiding it through the corresponding opening to the tensioning device and then threading this end on there.

In other words, this procedure of fixing the plate-like bodies, for example on the skin, and joining them together can be carried out very easily.

In a further configuration of the invention, on one side there is more than one plate-like body, respectively joined to a plate-like body arranged lying opposite by means of a pulling thread in each case.

If, for example, a lesion is relatively large or of a correspondingly irregular or curved shape, it is not only possible for one plate-like body to be respectively placed on both sides of the lesion but for a number of plate-like bodies to be placed on, but these have to be respectively fixed to the skin and joined to one another subcutaneously.

In this way, such lesions can also be dealt with very flexibly and corresponding stretchings of the skin can be accomplished.

In a further configuration of the invention, one plate-like body has a tensioning device and this plate-like body is joined to a number of plate-like bodies on an opposite side by means of a pulling thread in each case, and the pulling threads of the number of plate-like bodies are guided by the thread guidance to a single tensioning device and can be tensioned simultaneously by this single tensioning device.

This measure has the advantage that all the threads can be tensioned simultaneously by means of a single tensioning device, to which the number of threads are fed from the number of oppositely lying plate-like bodies. This makes handling easier, particularly if this is carried out independently by the patient.

In a further configuration of the invention, two plate-like bodies disposed lying opposite are joined by means of two separate pulling threads in each case.

This measure has the advantage that the separate pulling threads provide the possibility of pulling more strongly on one pulling thread than on the other, so that it is possible to change the alignment of the plate-like bodies to one another during the stretching of the tissue. This may be desirable if more regions of tissue are available for stretching at one end region of such a plate-like body than, for example, at another end region of such a plate-like body.

In a further configuration of the invention, each separate pulling thread is assigned a separate tensioning device.

This measure has the advantage, if desired, of imparting a tensioning force individually to each individual pulling thread, it being possible for this to be carried out with these separate tensioning devices.

This measure can be taken in particular when in the case of lesions of a very large surface area and irregularly shaped lesions there are regions of surrounding skin that are much more accessible for stretching than other regions of skin. The different tensioning devices then allow separate plate-like bodies to be placed in these different regions as a counterpart and allow the skin to be correspondingly stretched differently by the different actuation by means of the tensioning device.

In a further configuration of the invention, the separate pulling threads may be fed by the thread guidance to a single tensioning device and are tensioned by it.

This measure has the advantage that, if there are a number of tensioning threads as already mentioned above, they can be tensioned by means of a single tensioning device.

In a further configuration of the invention, two oppositely lying plate-like bodies can be moved towards one another in the plane of their plates.

This measure has the advantage in particular when stretching skin that the two plate-like bodies are applied flat to the skin and are moved towards one another in the plane of their plates. The tissue present between the plate-like bodies that can be moved towards one another is compressed, the tissue lying "behind" in the direction of movement is stretched.

In a further configuration of the invention, the at least one first plate-like body can be placed onto the skin on one side of a lesion and the at least one second plate-like body can be placed onto the skin on another, opposite side of the lesion, and the two plate-like bodies can be respectively joined to the skin and also joined together subcutaneously.

This measure has the advantage that both the fixing of the plate-like bodies to the skin and the joining of the two plate-like bodies together can be accomplished by a very simple procedure that can be carried out in a minimally invasive manner. Thus, for example, the pulling thread can be guided by means of an awl from the one body subcutaneously to the other plate-like body and back again in order thereby to accomplish the tensile joining.

In a further configuration of the invention, the plate-like bodies are produced from a formable material.

This measure has the advantage that, in the case of curved regions of tissue, the plate-like bodies can be individually adapted to the corresponding curvature. This may take place on the one hand by the plate-like bodies themselves consisting of a deformable material. On the other hand, it is also possible first to make impressions of the correspondingly curved regions of tissue and then to use these impressions to shape the plate-like bodies if, for example, a vessel is to be stretched because it has been shortened as a result of an injury, the plate-like bodies can be adapted exactly to the curvature of the vessel.

In a further configuration of the invention, the plate-like bodies are curved in a way corresponding to the regions of tissue.

This measure has the advantage that the plate-like bodies lie correspondingly flush on the tissue, and consequently the tensile force is exerted on the tissue in an evenly distributed manner.

In a further configuration of the invention, the tensioning device is rotatable, it being possible for at least one pulling thread to be wound up.

This configuration, which is known from the document mentioned at the beginning, has the advantage that the tensioning procedure can be carried out with a compact construction and a device that is easy to operate, and the pulled-in thread is stored right away in a space-saving manner.

In a further configuration of the invention, the tensioning device has a latching mechanism which blocks turning of the tensioning device counter to a pulling-thread tensioning force.

This measure, which is likewise known per se, has the advantage that the patient independently turns the tensioning device by a specific number of detents or teeth in the tensioning direction, but turning back is blocked by the latching mechanism.

For setting up the device, that is to say for placing the thread and later detaching the thread, a corresponding mechanism may then be provided in order to deactivate this latching mechanism.

In a further configuration of the invention, the tensioning device protrudes from one side of the plate-like body and can be operated by hand.

This measure has the handling advantage that the tensioning device does not adversely affect the contact locations of the plate-like bodies on the tissue and the tensioning device is easily accessible to manipulate for tensioning the thread. The term "can be operated by hand" also means that the patient can use an implement to help with the turning, but the patient him/herself controls the tensioning of the pulling thread.

BRIEF DESCRIPTION OF THE DRAWINGS

It goes without saying that the features mentioned above and those still to be explained below can be used not only in the combinations respectively specified but also in other combinations or on their own without departing from the scope of the present invention.

The invention is described in more detail and explained below on the basis of some selected exemplary embodiments in conjunction with the accompanying drawings, in which.

DETAILED DESCRIPTION OF PREFERRED EXEMPLARY EMBODIMENTS

A first exemplary embodiment, represented in FIGS. 1 to 4, of a device according to the invention for stretching regions of skin on both sides of a lesion to be excised is designated as a whole by the reference numeral 10.

Figure 1:
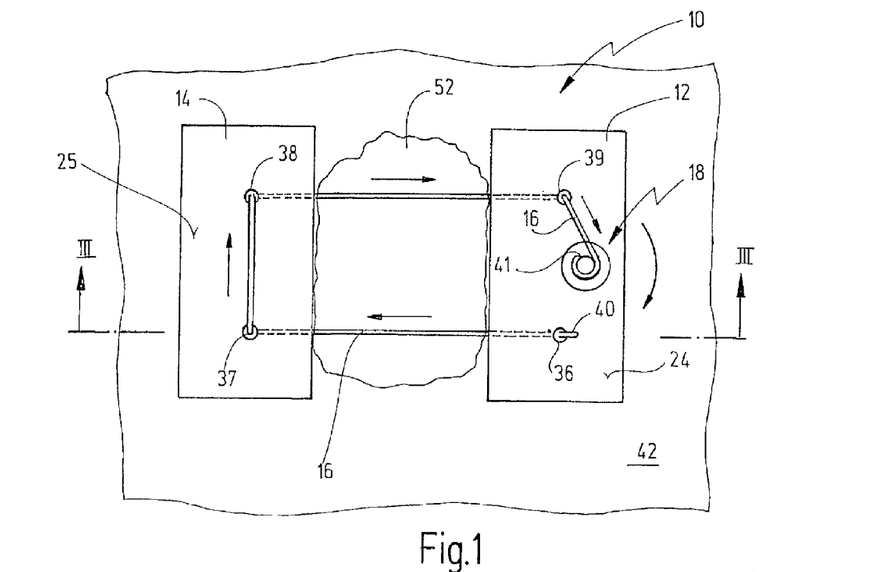
FIG. 1 shows highly schematically a plan view of a first exemplary embodiment of a device according to the invention for stretching the skin, which has already been placed on the skin on both sides of a lesion and fixed.

The device 10 has a first, approximately rectangular plate-like body 12 and a second, planar plate-like body 14 of approximately the same size.

Both plate-like bodies 12 and 14 are produced from medical-grade steel. Plastics, such as those used in dental prosthetics, may also be used. A pulling thread 16 joins the two plate-like bodies 12 and 14 to one another, one end 41 of the pulling thread 16 being fixed to a tensioning device 18 standing up on the upper side 24 of the first plate-like body 12. The other end 40 is likewise fixed to the plate-like body 12.

Figure 3:
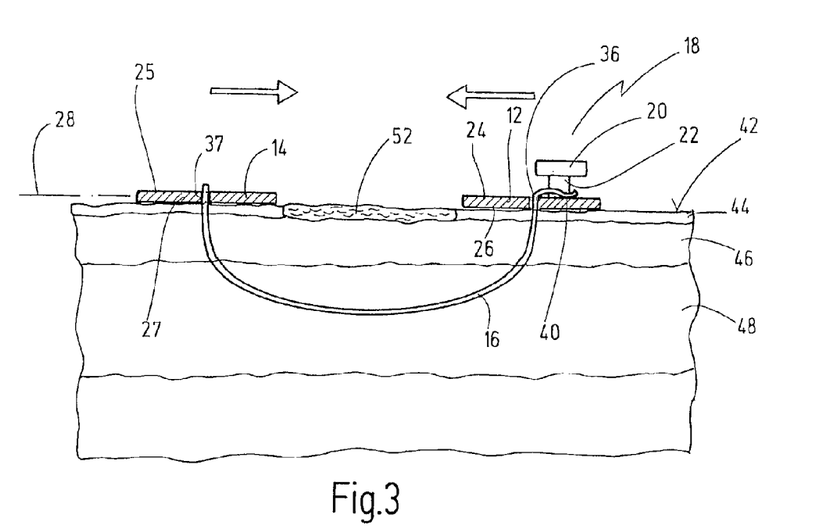
FIG. 3 shows a section along the line in FIG. 1.

As can be seen in particular from FIG. 3, the tensioning device 18 has an outer turning knob 20, which is connected to a hub 22. Fixed to the hub 22 is the end 41 of the pulling thread 16, and turning of the turning knob 20 causes turning of the hub 22 and winding-up of the pulling thread 16 onto the tensioning device 18. As can be seen in particular from FIG. 3, both plate-like bodies 12 and 14 lie with their respective underside 26 and 27 flat on a skin 42 on both sides of a lesion 52, that is to say both extend approximately in a plane of the plates 28.

As can be seen in particular from FIG. 1, the two plate-like bodies 12 and 14 are placed in such a way that they are aligned approximately parallel to one another, so that the two oppositely lying longitudinal edges are approximately mutually parallel. By means of the thread guidance to be described below, the two plate-like bodies 12 and 14 are joined together and respectively joined to the skin 42.

Figure 2:
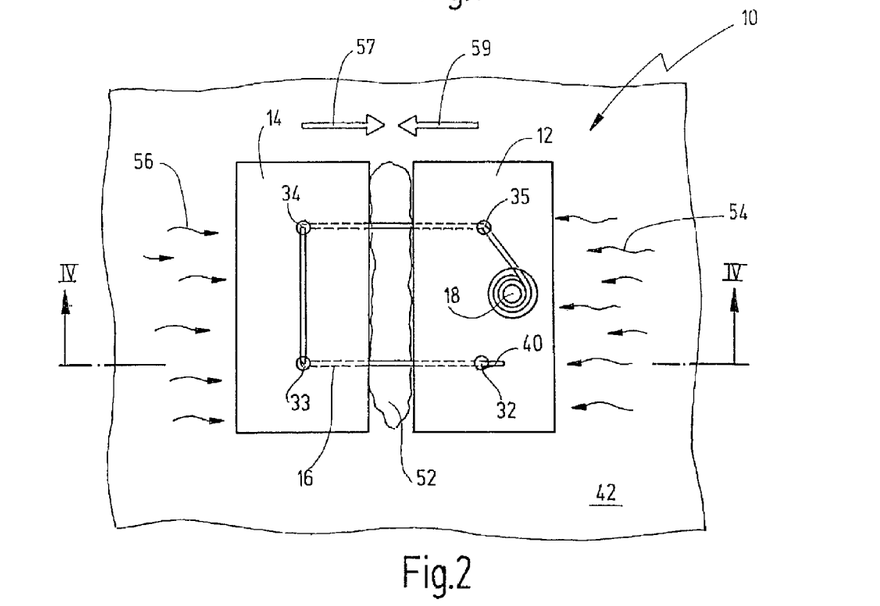
FIG. 2 shows a plan view comparable to FIG. 1 after completion of the skin stretching procedure.

For this purpose, as designated in particular in FIG. 2, provided on the first plate-like body 12 is a first fixing location 32, in the region of which a first end 40 of the pulling thread 16 is fixed. This fixing takes place on the upper side 24 of the plate-like body 12. It can be seen from FIGS. 1 and 3 that a round opening 36, passing through the first plate-like body 12, is provided in the region of this fixing location 32.

Through this opening 36, which has rounded-off edges, the pulling thread 16 is guided from the fixing location 32 through the plate-like body 12 from the upper side 24.

The fixing of the end of the thread 40 may either be performed by it being fastened by means of a rivet or the like to be applied, or by this end of the thread 40 quite simply being knotted a number of times, so that the knot cannot then pass through the opening 36.

As can be seen in particular from FIGS. 1 and 3, provided on the second plate-like body 14, lying opposite the first plate-like body 12, approximately at the same position, is a corresponding opening 37, through which the pulling thread 16 can be guided through the plate-like body 14 from the underside 27. The pulling thread 16 is guided from the opening 36 in the first plate-like body 12 to the opening 37 in the second plate-like body 14 subcutaneously, as can be seen in particular from the sectional representation of FIG. 3, i.e. the pulling thread 16 is inserted through the epidermis 44 and the dermis 46 into the subcutaneous fatty tissue 48 and guided through under the lesion 52 to the underside 27 of the second plate-like body 14.

As can be seen in particular from FIG. 1, in the second plate-like body 14 there is also a second opening 38, through which the pulling thread 16 can, be guided again from the upper side 25 through the second plate-like body 14. This portion of thread is then also returned in the way described above subcutaneously to the first plate-like body 12 and passes there through an opening 39 from the underside 26 through the first plate-like body 12, and is then threaded at its second end 41 onto the hub 22. The opening 39 consequently acts as a guiding location 35 for the guiding of the pulling thread 16 out or through the first plate-like body 12.

It can be seen from the plan view of FIG. 1 that, in the case of this arrangement of the first and second plate-like bodies 12 and 14, the four openings 36, 37, 38, 39 lie at the corners of a rectangle.

The two openings 37 and 38 in the second plate-like body 14 act as abutments 33 and 34 when a tensile force is exerted on the pulling thread 16 by means of the tensioning device 18.

The plate-like bodies may also have a number of such openings, consequently may be produced as perforated plates, so that different openings can be used for the thread guidance, according to the circumstances. Consequently, a plate-like body with a multi-hole pattern can be used for lesions of different sizes or shapes.

This takes place when, in the case of the assembly of the device 10 that is represented in FIG. 1, the turning knob 20 is moved clockwise, as indicated by an arrow. Since both ends of the thread 41 and 40 are fixed on the first plate-like body 12, the tensile force causes the two plate-like bodies 12 and 14 to be moved towards one another, so that a state such as that represented in FIG. 2 is reached.

This means that both plate-like bodies 12 and 14 have moved towards one another, as indicated by the arrows 57 and 59 in FIG. 2.

The regions of skin 54 and 56 situated "behind" in the respective direction of movement (arrows 57 and 59) of the plate-like bodies 12 and 14 are thereby stretched, which is the essential purpose of the device 10.

Figure 4:
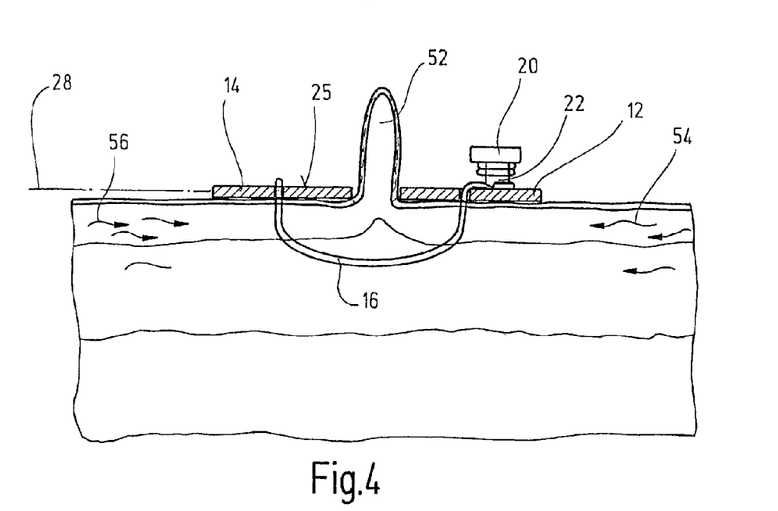
FIG. 4 shows a section along the line IV-IV in FIG. 2.

At the same time, as can be seen in particular from FIGS. 2 and 4, the region of the skin situated between the edges of the plate-like bodies 12 and 14 that are running towards one another, namely the region of the lesion 52, is compressed or squeezed. In the excision, this region can then be simply gripped and cut away.

The transition from FIG. 1 to FIG. 2 may be achieved gradually within several days, in that the turning knob 20 is gradually moved increasingly clockwise.

With respect to the more specific structural configuration of the tensioning device 18, reference is expressly made to the tensioning device such as is described in DE 103 49 953 A1, i.e. the design described there is explicitly included as disclosure in the present application. Consequently, there is also a latching mechanism, not represented any more specifically here, which prevents the turning knob 20 from turning anticlockwise on account of the tensioning force.

Once the two plate-like bodies 12 and 14 have been placed on a patient in the way represented in FIG. 1 and have been joined both to the skin 42 and together by the pulling thread 16, a specific regime as to how much and how often the patient is to move the turning knob 20 in the coming days until the situation represented in FIG. 2 is reached is prescribed by the doctor.

Since no further interventions in the body are necessary for this and the turning knob 20 is easily accessible for the patient, said patient can carry this out him/herself without iatric support.

During the excision of the lesion, the plate-like bodies 12 and 14 are then removed again, for which purpose the pulling thread 16 is detached and discarded. After cleaning and sterilizing, the device 10 is ready for further use.

Figure 5:
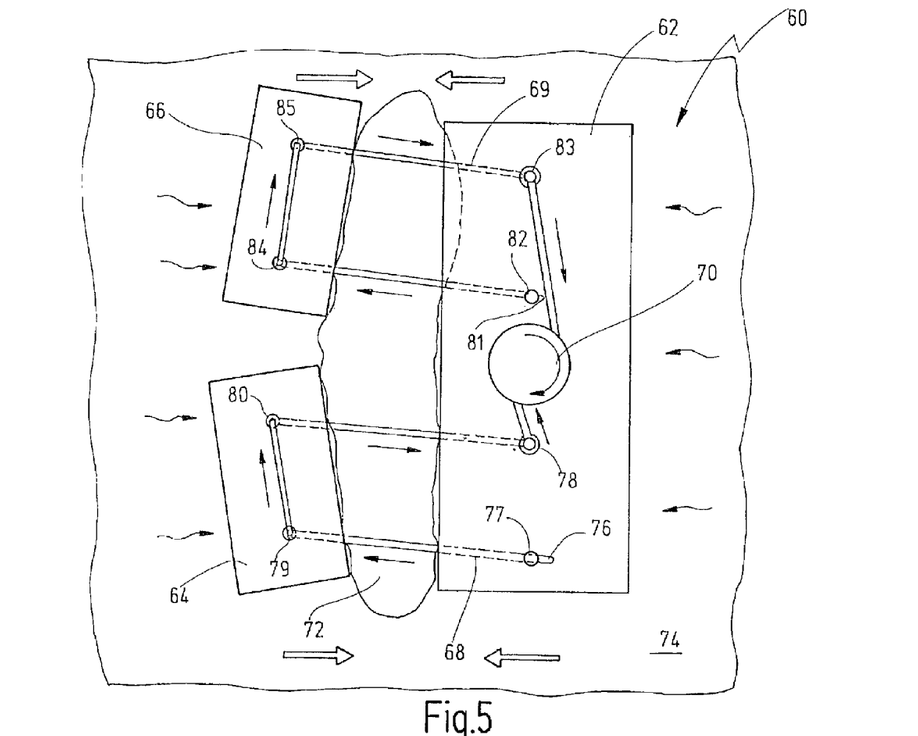
FIG. 5 shows a representation comparable to the representation of FIG. 1 of a second exemplary embodiment of a device for stretching regions of skin in which two plate-like bodies have been placed on one side.

In FIG. 5, a second exemplary embodiment of a device according to the invention is shown, designated as a whole by the reference numeral 60.

This device 60 also operates in principle in the same way as the first exemplary embodiment described above, and is accordingly fixed on the skin 74 of a patient.

By contrast with the device 10 described above, in the case of the device 60 there is a relatively large first plate-like body 62, which is likewise rectangular and is placed on one side of a relatively long lesion 72.

By contrast with the exemplary embodiment described above, two plate-like bodies 64 and 66, which are approximately only half the size of the first plate-like body 62, are placed on the side of the lesion opposite from the plate-like body 62. It can be seen from FIG. 5 that the lesion has a curved contour, so that the two edges of the second and third plate-like bodies 64 and 66 that lie opposite the edge of the first plate-like body 62 that is lying against the lesion 72 consequently run obliquely in relation to that edge.

As described above, the second plate-like body 64 is joined to the first plate-like body 62 by means of a pulling thread 68. The third plate-like body 66 is joined to the first plate-like body 62 by means of a further pulling thread 69.

Here, too, the thread guidance is then again such that a first end of the pulling thread 68 is fixed at a fixing location 76, this thread is guided through a first opening 77 through the first plate-like body 62 and is then guided subcutaneously to a first opening 79 in the second plate-like body 64. As described above, this pulling thread 68 is then guided over the upper side of the second plate-like body 64 to the second opening 80 and then guided through the plate and subcutaneously to the opening 78 in the first plate-like body 62. From this opening, the end of the thread is then guided to a tensioning device 70, fixed there and threaded on.

Correspondingly, the second pulling thread 69 is guided from a fixing location 81 by way of an opening 82 in the first plate-like body 62 subcutaneously to a first opening 84 in the third plate-like body 66, is guided there over the surface thereof to the second opening 85 in the third plate-like body 66 and is guided through the latter and subsequently guided subcutaneously to a fourth opening 83 in the first plate-like body 62. The second pulling thread 69 emerges from this opening 83 and is likewise fed to the tensioning device 70.

Clockwise turning of the tensioning device 70, as indicated by an arrow, has the effect that both tensioning threads 68 and 69 are tensioned or wound up, so that a tensile force is exerted on both plate-like bodies 64 and 66. Here, too, the openings 79 and 80 or 84 and 85 in the plate-like bodies 64 and 66 again serve as corresponding abutments. Here, too, a movement of the first plate-like body 62 on the one hand and the two plate-like bodies 64 and 66 on the other hand towards one another takes place, whereby the desired stretching of the skin is then achieved.

The functional principle is the same as described above, it is just that here a number of counterparts in the form of the plate-like bodies 64 and 66 are used on account of the geometry of the lesion.

It is obvious that, in the case of correspondingly longer or different shapings of a lesion 72, more than two or geometrically differently formed plate-like bodies 64 and 66 may also be used.

It is also possible to place two devices 10, such as are described above, on the relatively long lesion 72 of FIG. 5.

It will be appreciated that very many structural configurations are possible here to allow adaptation as individually as possible to the nature of the skin and the lesion, while the same basic principle is always used as a basis.

Figure 6:
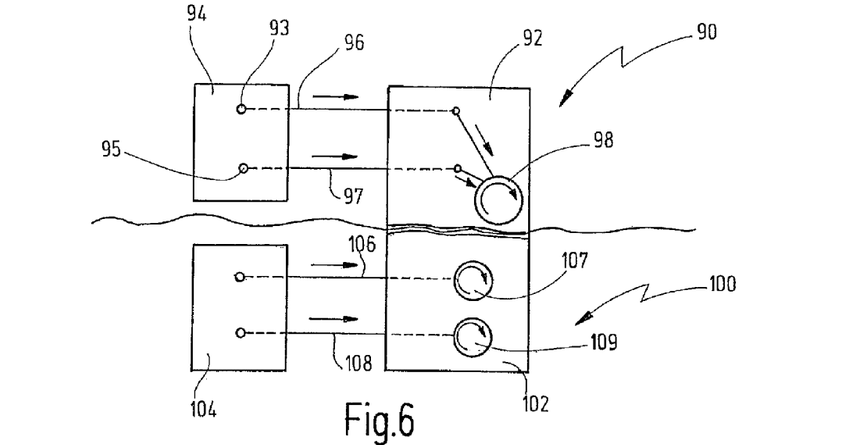
FIG. 6 shows in the upper half a third exemplary embodiment of a device for stretching regions of skin, in which the two oppositely lying plate-like bodies are joined by means of separate pulling threads in each case, which are wound up onto a single tensioning device, and shows in the lower half a fourth exemplary embodiment, in which each thread is fed to its own assigned tensioning device.

In the case of the further exemplary embodiments represented in FIG. 6, represented on the upper half is a device 90, which in principle is initially constructed in the same way as the exemplary embodiment of FIG. 1, i.e. there is a first plate-like body 92 opposite which there lies a second plate-like body 94. By contrast with the first exemplary embodiment, here in the case of the third exemplary embodiment there are two separate pulling threads 96 and 97, which are respectively fed to one and the same tensioning device 98 on the first plate-like body 92. The other ends respectively of the pulling threads 96 and 97 are fixed at the corresponding openings 93 and 95 in the second plate-like body 94, for example by a knot.

In the case of the first configuration, represented in FIG. 1, with only a single pulling thread, during tensioning the pulling thread 16 runs over the upper side 25 of the second plate-like body 14. That is to say such a portion of the pulling thread 16 passes by way of the opening 38 through the second plate-like body 14 and into the subcutaneous tissue.

Therefore, appropriate measures must be provided to ensure that this portion of thread between the abutments or openings 37 and 38 cannot be contaminated and possibly cause an infection. Appropriate disinfecting or covering measures must be provided or an inner channel in which the portion of thread is guided in a sterile manner must be provided in the second plate-like body 14, in order to minimize such a risk of infection.

In the case of the design shown on the upper half in FIG. 6, this is not necessary since here there are two separate pulling threads 96 and 97, one end of which in each case is fixed at the openings 93 and 95.

In FIG. 6, represented on the lower half is a fourth exemplary embodiment of a device 100 according to the invention, which in principle is of the same construction as the device 90 and also the devices described above and is fastened to the skin, with the difference that the two individual pulling threads 106, 108 are respectively fed to a single tensioning device 107, 109 on the first plate-like body 102. This makes it possible to exert a different tensile force on the pulling thread 106 by means of the tensioning device 107 than on the pulling thread 108 by means of the tensioning device 109, with the consequence that the second plate-like body 104 can, for example, be tilted or set obliquely in the course of the movement, should this be advisable or necessary for certain reasons in order to achieve the desired stretching of the skin.

To sum up, it can be said that numerous configurations of the device according to the invention are possible in order to adapt individually to the local circumstances in the region of the skin and the lesion, but all are based on the same basic principle.

This basic principle is the simple construction provided by the plate-like bodies and the easy fixing of these bodies to the skin and their joining together by means of the subcutaneous thread guidance.

What is claimed is:

1. A device for stretching regions of tissue, comprising:
   multiple plate-like bodies, said plate-like bodies being arranged lying opposite on a tissue to be stretched,
   at least one pulling thread joining said oppositely arranged plate-like bodies,
   at least one tensioning device arranged on at least one of said plate-like bodies, said tensioning device being connected to said at least one pulling thread and serves for applying a tensile force to said at least one pulling thread, and
   a thread guidance being disposed on said plate-like bodies for guiding said at least one pulling thread joining said plate-like bodies, said guidance serves for guiding a movement of said plate-like bodies towards one another when said pulling thread is tensioned by said at least one tensioning device;
   wherein a plurality of said plate-like bodies is adapted for attaching on one side of opposite sides of said tissue and a single plate-like body of said plate-like bodies is adapted for attaching on an opposing side of said opposite sides, said single plate-like body having said at least one tensioning device, each of said plurality of said plate-like bodies being joined to said single plate-like body by a separate pulling thread; and
   wherein said single plate-like body, having arranged said tensioning device thereon, has at least one guiding location by means of which each pulling thread is fed to said tensioning device and is wound up there at a first end of each pulling thread, and having at least one fixing location for a second end of each pulling thread, and wherein at least one of said plate-like bodies lying opposite to said single plate-like body has at least two abutments spaced laterally apart from one another, wherein said abutments, said at least one fixing location and said at least one guiding location are shaped as openings in said plate-like bodies, said pulling thread being guided across a plane of said plate-like bodies through said openings.

2. The device of claim 1, wherein said thread guidance, on a plate-like body lying opposite to said single plate-like body on which said tensioning device is arranged, has two abutments spaced laterally apart from one another.

3. The device of claim 1, wherein said thread guidance, on said single plate-like body having arranged said tensioning device, has at least one guiding location, by means of which said at least one pulling thread is fed to said tensioning device and is wound up there at a first end of said at least one pulling thread.

4. The device of claim 1, wherein said thread guidance, on said single plate-like body having arranged said tensioning device, has at least one fixing location for a second end of said at least one pulling thread.

5. The device of claim 1, wherein said single plate-like body, having arranged said tensioning device thereon, has at least one guiding location by means of which each pulling thread is fed to said tensioning device and is wound up there at a first end of each pulling thread, and has at least one fixing location for a second end of each pulling thread, and wherein at lest one of said plate-like bodies lying opposite to said single plate-like body has two abutments spaced laterally apart from one another, wherein said two abutments, said at least one guiding location and said at least one fixing location lie at corners of a quadrilateral.

6. The device of claim 1, wherein said single plate-like body, having arranged thereon said tensioning device, is joined to said plate-like bodies arranged opposite to said single plate-like body by separate pulling threads, and wherein said separate pulling threads are each guided by said thread guidance to said single tensioning device and are tensioned simultaneously by said single tensioning device.

7. The device of claim 1, wherein said single plate-like body and at least one of said plurality of said plate-like bodies are adapted to move towards one another in a common plane.

8. The device of claim 1, wherein said plurality of said plate-like bodies is placed on a skin on one side of a lesion, and wherein said single plate-like body is placed on an opposite side of said lesion, and wherein said opposite plate-like bodies are connected to both said skin and together subcutaneously.

9. The device of claim 1, wherein said plate-like bodies having a plate extending in an even plane.

10. The device of claim 1, wherein said plate-like bodies having a plate having a curved plane, which curved plane being adapted to a curvature of said tissue.

11. The device of claim 1, wherein said plate-like bodies are made of a formable material.

12. The device of claim 1, wherein said tensioning device is rotatable, said at least one pulling thread being wound up on said rotatable tensioning device when turned.

13. The device of claim 1, wherein said tensioning device being provided with a latching mechanism, said latching mechanism blocking said tensioning device moving counter to a tensioning force tensioning said pulling thread.

14. The device of claim 1, wherein said tensioning device protrudes from one side of said single plate-like body.

15. The device of claim 1, comprising more than one of said plate-like bodies lying opposite to one or more of said plate-like bodies, each of said more than one of said plate-like bodies being connected to the one or more of said plate-like bodies by a separate pulling thread.

16. The device of claim 15, wherein each of said separate pulling thread is fed by a thread guidance to a single tensioning device and all of said separate pulling threads can be tensioned by said single tensioning device.

17. The device of claim 15, wherein each separate pulling thread is connected to a separate tensioning device.

* * * * *